(12) United States Patent
Yodfat et al.

(10) Patent No.: US 8,970,384 B2
(45) Date of Patent: Mar. 3, 2015

(54) DEVICES AND METHODS FOR MALFUNCTIONS RECOGNITION IN A THERAPEUTIC DISPENSING DEVICE

(75) Inventors: Ofer Yodfat, Modi'in (IL); Zohar Man, Haifa (IL); Tsabar Mor, Naharia (IL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 377 days.

(21) Appl. No.: 13/377,906

(22) PCT Filed: Jun. 14, 2010

(86) PCT No.: PCT/IL2010/000467
§ 371 (c)(1),
(2), (4) Date: Apr. 19, 2012

(87) PCT Pub. No.: WO2010/146579
PCT Pub. Date: Dec. 23, 2010

(65) Prior Publication Data

US 2012/0192951 A1     Aug. 2, 2012

Related U.S. Application Data

(60) Provisional application No. 61/186,858, filed on Jun. 14, 2009.

(51) Int. Cl.
*G08B 21/00* (2006.01)
*A61M 5/168* (2006.01)
(Continued)

(52) U.S. Cl.
CPC ......... *A61M 5/16831* (2013.01); *A61M 5/1456* (2013.01); *A61M 2005/14268* (2013.01); *A61M 2005/16863* (2013.01)
USPC ........... 340/603; 340/573.1; 604/67; 604/151

(58) Field of Classification Search
CPC ......... G01F 1/363; G01F 1/372; G01F 1/383; A61M 2005/16863; A61M 2005/16868; A61M 2005/16872; A61M 5/1413; A61M 5/1456; A61M 5/14566; A61M 5/16854; A61M 5/1684; A61M 5/486; A61M 5/172

USPC .......... 340/573.1, 648, 603, 626, 636.1, 679; 604/65, 66, 67, 151, 153, 155, 156, 604/250; 73/1.36, 168, 290 R; 137/1, 551
See application file for complete search history.

(56) References Cited

U.S. PATENT DOCUMENTS

| 5,957,895 A | 9/1999 | Sage et al. |
|---|---|---|
| 6,248,093 B1 | 6/2001 | Moberg |

(Continued)

FOREIGN PATENT DOCUMENTS

| WO | WO-9707843 A1 | 3/1997 |
|---|---|---|
| WO | WO/2007/052277 A1 | 5/2007 |

(Continued)

OTHER PUBLICATIONS

International Search Report for PCT Application No. PCT/IL2010/00467, date of mailing of search report Oct. 27, 2010.

(Continued)

*Primary Examiner* — Anh V La
(74) *Attorney, Agent, or Firm* — Roche Diagnostics Operations, Inc.

(57) ABSTRACT

Disclosed are systems, devices, and methods, including a system that includes a sensor configured to monitor at least one parameter associated with operation of the fluid delivery device, and a controller. The controller is configured to activate a motor of the fluid delivery device, detect an occurrence of a problem in fluid delivery based on one or more first sensor signals generated by the sensor when the motor is activated in a first direction, the one or more first sensor signals representative of the at least one parameter monitored in the first direction, and determine a type of the detected problem based on one or more second sensor signals generated by the sensor when the motor is activated in a second direction substantially opposite the first direction, the one or more second sensor signals representative of the at least one parameter monitored in the second direction.

22 Claims, 8 Drawing Sheets

(51) Int. Cl.
*A61M 5/145* (2006.01)
*A61M 5/142* (2006.01)

(56) References Cited

U.S. PATENT DOCUMENTS

| | | | |
|---|---|---|---|
| 6,362,591 B1 | 3/2002 | Moberg | |
| 6,485,461 B1 | 11/2002 | Mason et al. | |
| 6,555,986 B2 | 4/2003 | Moberg | |
| 6,589,229 B1 | 7/2003 | Connelly et al. | |
| 6,723,072 B2 | 4/2004 | Flaherty et al. | |
| 6,740,059 B2 | 5/2004 | Flaherty | |
| 7,193,521 B2 | 3/2007 | Moberg et al. | |
| 7,390,314 B2 | 6/2008 | Stutz, Jr. et al. | |
| 8,182,461 B2 * | 5/2012 | Pope et al. | 604/503 |
| 8,223,028 B2 * | 7/2012 | Mandro et al. | 340/626 |
| 2002/0043951 A1 | 4/2002 | Moberg | |
| 2003/0205587 A1 | 11/2003 | Tribe et al. | |
| 2006/0184154 A1 | 8/2006 | Moberg et al. | |
| 2007/0106218 A1 | 5/2007 | Yodfat et al. | |
| 2007/0112301 A1 | 5/2007 | Preuthun et al. | |
| 2007/0191702 A1 | 8/2007 | Yodfat et al. | |
| 2008/0214916 A1 | 9/2008 | Yodfat et al. | |
| 2008/0215035 A1 | 9/2008 | Yodfat et al. | |
| 2008/0294094 A1 * | 11/2008 | Mhatre et al. | 604/65 |

FOREIGN PATENT DOCUMENTS

| | | |
|---|---|---|
| WO | WO/2007/093921 A2 | 8/2007 |
| WO | WO/2008/078318 A2 | 7/2008 |
| WO | WO/2008/139459 A1 | 11/2008 |
| WO | WO/2009/013736 A1 | 1/2009 |
| WO | WO/2009/016636 A2 | 2/2009 |
| WO | WO/2008/078319 A1 | 7/2009 |
| WO | WO/2009/125398 A2 | 10/2009 |

OTHER PUBLICATIONS

Written Opinion of the International Searching Authority for PCT Application No. PCT/IL2010/00467, date of mailing Oct. 27, 2010.

* cited by examiner

DEVICES AND METHODS FOR MALFUNCTIONS RECOGNITION IN A THERAPEUTIC DISPENSING DEVICE

CROSS-REFERENCE TO RELATED APPLICATION

The present application is a 35 U.S.C. §371 national stage entry of PCT/IL2010/000467, which has an international filing date of Jun. 14, 2010, and claims benefit and priority to U.S. Provisional Patent Application No. 61/186,858, filed on Jun. 14, 2009, entitled "Devices and Methods for Malfunctions Recognition in a Therapeutic Dispensing Device", the contents of which are hereby incorporated by reference in their entireties.

FIELD

Embodiments of the present disclosure are directed to systems, devices and methods for sustained delivery of fluids and/or continuous monitoring of a body analyte. More particularly, some embodiments of the present disclosure are directed to portable skin adherable/affixable infusion devices, and to systems, devices and methods for detecting occlusion and/or device malfunctions.

BACKGROUND

Medical treatment of many illnesses requires continuous (or periodic) drug infusion into various parts of the body via subcutaneous and/or intravenous injections. Diabetes mellitus patients, for example, require the administration of varying amounts of insulin throughout the day to control their blood glucose levels. In recent years, ambulatory portable insulin infusion pumps, employing continuous subcutaneous insulin infusion (CSII), have emerged as a superior alternative to multiple daily injections (MDI) of insulin for Type 1 and Type 2 diabetes patients using syringes. These pumps, which deliver insulin at a continuous basal rate, as well as in bolus volumes, were developed to liberate patients from repeated self-administered injections, and allow them to maintain a near-normal daily routine. Both basal and bolus volumes must be delivered in precise doses, according to individual prescription, because an overdose or underdose of insulin could be fatal.

Insulin Pumps Evolution

The first generation of portable insulin pumps includes a "pager like" device with a driving mechanism including motor and gears, and a reservoir contained within a housing. Examples of such devices are described, for example, in U.S. Pat. Nos. 6,248,093 and 7,390,314. In conventional configurations, a driving mechanism, which includes a motor, a gear and a drive screw, moves a plunger inside a syringe (reservoir) to deliver insulin into the user's body. For example, as the motor rotates a gear, a threaded drive screw is rotated. The plunger of the syringe has an elongated member shaped like a cylinder which is internally threaded for engagement with the drive screw. As a result, the motor rotates the drive screw which engages the threads of the cylinder and converts the rotation of the drive screw into a linear motion to displace the plunger in an axial direction. These first generation devices represent a significant improvement over multiple daily injections (MDI), but are typically large sized, heavy weighted, and have long tubing.

To ease the use of portable insulin pumps, second generation pumps were proposed. Second generation pumps are based on use of a remote-controlled skin adherable device having a bottom surface adapted to be in contact with a patient's skin. A reservoir is contained within the housing and can be filled using an additional syringe. The additional syringe is used to draw medicine from a vial and then inject the medicine into the reservoir. This concept is discussed, for example, in U.S. Pat. Nos. 5,957,895, 6,589,229, 6,740,059, 6,723,072, and 6,485,461. These second generation devices generally have to be disposed of every 2-3 days (e.g., due to insertion site infections and reduced insulin absorption), including all the expensive components, such as electronics and the driving mechanism.

A third generation pump was developed to avoid the cost issues associated with the second generation devices and to expand patient customization. An example of a third generation device is disclosed, for example, in co-owned, co-pending U.S. Patent Application Publication No. 2007-0106218, and in co-owned International Patent Application Publication No. WO/2007/052277, the contents of all of which are hereby incorporated by reference in their entireties. Such a third generation device contains a remote control unit and a skin-adherable patch unit that may include two parts: (1) a reusable part containing the electronics, at least a portion of the driving mechanism and other relatively expensive components, and (2) a disposable part containing the reservoir and, in some embodiments, at least one power source (e.g., a battery).

A further improvement to the skin adherable pump that includes two parts is described, for example, in co-owned, co-pending U.S. Patent Application Publication No. 2008-0215035 and in co-owned International Patent Application Publication No. WO/2008/078318, the contents of all of which are hereby incorporated by reference in their entireties. The disclosed device is configured as a dispensing unit that can be disconnected from and reconnected to a skin-adherable cradle unit. Such skin-securable dispensing units can be remotely controlled and/or operated by a user interface (e.g., a buttons-based interface) provided on a housing of the dispensing unit, as disclosed, for example, in co-owned International Patent Applications Publication Nos. WO/2009/013736 and WO/2009/016636, the contents of all of which are hereby incorporated by reference in their entireties.

An insulin infusion device may be integrated with a continuous glucose monitor (CGM) enabling open and/or closed loop systems. Such a device integrating insulin delivery and glucose monitoring is disclosed, for example, in co-owned, co-pending U.S. Patent Applications Publication Nos. 2007-0191702 and 2008-0214916, and in co-owned International Patent Applications Publication Nos. WO/2007/093981 and WO/2008/078319, the disclosures of which are incorporated herein by reference in their entireties.

Occlusion and Malfunctions Detection

An occlusion occurs when an infusion line (e.g., a tube, a cannula) is blocked. This is typically expressed as a kink in the infusion line, but in infusion lines delivering insulin, an occlusion may further occur because of insulin crystallization. Accordingly, an occlusion may cause under-infusion of insulin to the user's body, which may have significant health effects such as hyperglycemia. Most insulin pager pumps have an occlusion detection mechanism based on direct or indirect measurement of pressure elevation. When the therapeutic fluid (e.g., insulin) is to be delivered from a reservoir of the device into the user's body via a needle/cannula and an occlusion occurs, pressure is built up in the reservoir. Direct pressure measurement is the monitoring of force over the driving mechanism (pressure defined as force per unit area), while indirect pressure measurement relates to the monitoring of the motor's power (e.g., torque) or rotation of the motor shaft (also referred to as "motor rotation" or "rotation of the motor"). Pressure elevation hinders the rotation of the motor and/or gear (hereinafter "driving mechanism"), and may occasionally even cause cessation of motor operation. In other words, power provided to the motor will not result in rotation of the motor.

Occlusion detection by indirect pressure measurement is described, for example, in U.S. Pat. Nos. 6,362,591, 6,555, 986 and 7,193,521. In these examples, electrical current to an infusion pump's motor is measured and compared against a baseline average current, which must first be established when there is no occlusion condition. If the current exceeds a threshold, an occlusion alarm is triggered. According to these patents, measurement of current can also provide feedback to the controller of driving mechanism performance, with the aid of a driving mechanism rotation monitor (also referred to as an "encoder"), e.g., in case of a failure of the gearbox, the motor cannot rotate, the measured current is high and the encoder indicates that the driving mechanism is faulty. However, these references do not describe how to distinguish between an occlusion and a driving mechanism malfunction. Moreover, generally, when there is only one monitoring element (e.g., an encoder, current measurement), the controller cannot distinguish between an occlusion and a driving mechanism malfunction.

Other circumstances may also provide "occlusion-like" indications when only one monitoring mechanism is applied. Therefore, in order to distinguish occlusion related errors from other errors, at least two parameters related to the therapeutic fluid delivery generally have to be monitored. Typically, an encoder is used to monitor the driving mechanism and a separate monitoring mechanism is used for occlusion detection.

Such an occlusion monitoring/detection mechanism may include a pressure gauge, a flow meter, or a load cell, all of which take up space, and require additional power supply and dedicated signal/data processing. An example of such an occlusion monitoring/detection mechanism based on force measurements is described, for example, in U.S. Pat. No. 5,647,853.

The occlusion monitoring/detection mechanism may also malfunction and usually another monitoring instrument/device is required. For example, in U.S. Pat. No. 7,193,521, readings of a force sensor are compared to a position of the plunger to verify its proper condition.

SUMMARY

The present disclosure presents embodiments of systems, devices and methods to monitor operations of fluid dispensing devices and systems, and detect occlusion and device malfunctions, such as, for example, an inefficient motor, a broken gear or a stuck/jammed gear. For example, according to some embodiments, the motor's rotation and the motor's power consumption are compared. If there is no correlation (or relatively low correlation) between these two parameters (e.g., their ratio is outside a predetermined range), an error/problem is detected (the terms "error" and "problem" may be used interchangeably throughout this disclosure). The motor is then rotated backward, i.e., moved in the other direction. In some such embodiments, if during reverse rotation of the motor these parameters correlate (i.e., they have relatively high correlation, e.g., their ratio is within a predetermined range), the error may be identified as an occlusion (because the error is detected only in one direction, namely, during forward motion), and if there is no correlation (e.g., the determined correlation is relatively low), the error is recognized as a device malfunction (because the error is detected in both forward motion and backward motion). In some embodiments, detection of an error in both forward and backward motion may indicate that the operation of the driving mechanism is affected in both directions, and thus it may be determined that the error is related to a driving mechanism malfunction. It should be noted that the terms "no correlation" and "correlation" may be used in some embodiments to represent binary decisions (i.e., there is correlation or there is no correlation), or the terms may be used in some embodiments to represent relative values (e.g., "no correlation" could include relative low correlation, and "correlation" could include relatively high correlation).

In some embodiments, the driving mechanism of the fluid dispensing device includes a motor (e.g., a DC motor, a stepper motor, or a shape memory alloy motor) and at least one gear. In such embodiments, rotation of the motor may be monitored using an encoder, for example. Such an encoder may include, for example, an encoder propeller mounted on the motor shaft, and a light source (e.g., LED) and light detector (e.g., phototransistor), located on opposite sides of the encoder propeller. As the motor rotates, one or more fins of the encoder propeller periodically block the light emitted by the light source, and thus a number of rotations completed by the motor can be derived from signals generated by the light detector. In some embodiments, the light source may include electromagnetic sources (e.g., infrared sources), laser sources, and other electro-optic sources. Also, other energy sources may be used. The power consumption of the motor can be calculated based on the number of pulses provided to the motor by a motor driver, for example, in case the motor is activated discretely by series of pulses (e.g., a stepper motor), where at least one of the voltage and current of the pulses is determined by the motor driver and/or the device controller. In some embodiments, the motor's power consumption can be derived/measured using additional components, such as a fuel gauge, a current limiter, or a DC-to-DC converter, for example. It will be noted that for the purpose of this disclosure the terms "power consumption of the motor" and "power provided to the motor" may be used interchangeably, and refer to the power resulting in, or intended to result in, rotation of the motor.

In some embodiments, a fluid delivery device is disclosed. The fluid delivery device comprises a driving mechanism including a motor, and a sensor to monitor at least one parameter associated with the operation of the driving mechanism (e.g., rotation of the motor, fluid flow). In some embodiments, the driving mechanism may further include one or more gears. The fluid delivery device may further comprise a power source to provide power to at least the motor. The fluid delivery device may further include a controller. The controller may be configured to perform one or more of: activate the motor in a first direction, activate the motor in a second direction different from (e.g., substantially opposite) the first direction, receive one or more signals from the sensor corresponding to the monitored at least one parameter, process the one or more signals received from the sensor, determine a first ratio between a first value associated with the activation of the motor in the first direction and a second value associated with the at least one parameter monitored by the sensor and based on (e.g., derived from) at least one of the one or more sensor signals that is generated by the sensor when the motor is activated in the first direction, compare the first ratio to a first threshold, determine a second ratio between a third value associated with the activation of the motor in the second direction and a fourth value associated with the at least one parameter monitored by the sensor and based on (e.g., derived from) at least one of the one or more sensor signals that is generated by the sensor when the motor is activated in the second direction, compare the second ratio to a second threshold, and determine whether an occlusion condition or a device malfunction condition exists based on the comparison between the second ratio and the second threshold.

Embodiments of the device may include any of the following features noted below.

In some embodiments, a device for delivering a therapeutic fluid into a body of a patient is disclosed. The delivery device may comprise a driving mechanism including a motor. In some embodiments, the driving mechanism may further include one or more gears.

The delivery device may further include a sensor for monitoring an operation of the device. In some embodiments, the monitored operation is rotation of the motor. In some embodiments, the monitored operation is rotation of the one or more gears. The delivery device may further include a controller configured to perform one or more of: provide a first activation signal for activating (e.g., rotating) the motor in a first direction, provide a second activation signal for activating (e.g., rotating) the motor in a second direction substantially opposite the first direction, receive one or more first sensor signals from the sensor corresponding to the operation of the device when the motor is activated in the first direction, compare the one or more first sensor signals to the first activation signal (comparing the signals may include comparing parameters (or values) of the actual signals, comparing values which the signals are based on and/or comparing values which are derived from (or are based on) the signals), receive one or more second sensor signals from the sensor corresponding to the operation of the device when the motor is activated in the second direction, and compare the one or more second sensor signals to the second activation signal. In some embodiments, upon the controller comparing the one or more first sensor signals to the first activation signal and determining a mismatch between the first activation signal and the one or more first sensor signals (e.g., the ratio between the number of expected motor rotations, derived from, or otherwise based on, the first activation signal, and the number of executed motor rotations, derived from, or otherwise based on, the one or more first sensor signals, exceeds a predetermined threshold), the controller provides the second activation signal to the motor. In some embodiments, upon the controller comparing the one or more second sensor signals to the second activation signal and determining a match between the second activation signal and the one or more second sensor signals (e.g., the ratio between the number of expected motor rotations, derived from, or otherwise base on, the second activation signal, and the number of executed motor rotations, derived from, or otherwise based on, the one or more second sensor signals, does not exceed a predetermined threshold), an occlusion is determined to be detected.

Embodiments of the device may include one or more of the above-described features of the first device, as well as any of the following features noted below.

In some embodiments, upon the controller comparing the one or more second sensor signals to the second activation signal and determining a mismatch between the second activation signal and the one or more second sensor signals, a device malfunction is determined to be detected. In some embodiments, the detected device malfunction is a malfunction in a component of the driving mechanism (e.g., motor, gear).

In some embodiments, the first and/or second activation signals may include, inter alia, at least one of the following parameters: direction of activation (e.g., forward, in reverse), power parameters (e.g., voltage, current, time), amount of fluid to deliver and number of motor rotations.

In some embodiments, the controller is further configured to calculate the total number of occlusion detections.

In some embodiments, the controller is further configured to detect a device malfunction upon determining that a total number of occlusion detections exceeds a pre-determined value (i.e., a threshold).

In some embodiments, a method for malfunction recognition in a fluid delivery device is disclosed. The method includes providing power to activate (e.g., rotate) a motor of a fluid delivery device in a first direction to deliver the fluid (e.g., therapeutic fluid), receiving one or more first sensor signals from a sensor of the fluid delivery device which are generated during activation (e.g., rotation) of the motor in the first direction, processing the one or more first sensor signals, determining whether the one or more first sensor signals correlate with the power provided to activate the motor in the first direction, providing power to activate the motor in a second direction different from (e.g., substantially opposite) the first direction upon determining that the one or more first sensor signals do not correlate with the power provided to activate the motor in the first direction, receiving one or more second sensor signals which are generated during activation (e.g., rotation) of the motor in the second direction, processing the one or more second sensor signals, determining whether the one or more second sensor signals correlate with the power provided to activate the motor in the second direction and determining whether an occlusion or a device malfunction occurred based, at least in part, on a determination of whether the one or more second sensor signals correlate with the power provided to activate the motor in the second direction.

Embodiments of the method may include one or more of the above-described features of the devices, as well as any of the following features noted below.

Other embodiments of the method for malfunction recognition in a fluid delivery device may include: providing power to rotate a motor in a first direction to deliver the fluid (e.g., therapeutic fluid), monitoring (e.g., using a sensor) the rotation of the motor in the first direction, receiving one or more first sensor signals from a sensor which correspond to the rotation of the motor in the first direction, determining whether the one or more first sensor signals correlate with the power provided to rotate the motor in the first direction, calculating the total number of times it was determined that the one or more first sensor signals do not correlate with the power provided to rotate the motor in the first direction, determining whether the total number of times it was determined that the one or more first sensor signals do not correlate with the power provided to rotate the motor in the first direction exceeds a first threshold, providing power to rotate the motor in a second direction substantially opposite the first direction upon determining that the total number of times it was determined that the one or more first sensor signals do not correlate with the power provided to rotate the motor in the first direction exceeds the first threshold, monitoring the rotation of the motor in the second direction receiving one or more second sensor signals which correspond to the rotation of the motor in the second direction, determining whether the one or more second sensor signals correlate with the power provided to rotate the motor in the second direction, calculating the total number of times it was determined that the one or more second sensor signals do not correlate with the power provided to rotate the motor in the second direction, determining whether the total number of times it was determined that the one or more second sensor signals do not correlate with the power provided to rotate the motor in the second direction exceeds a second threshold, providing one of: an occlusion notification upon determining that the total number of times it was determined that the one or more second sensor signals do not correlate with the power provided to rotate the motor in the second direction does not exceed a second threshold, and a device malfunction notification upon determining that the total number of times it was determined that the one or more second sensor signals do not correlate with the power provided to rotate the motor in the second direction exceeds a second threshold.

Embodiments of the method may include one or more of the above-described features of the devices and/or of the first method, as well as any of the following features noted below.

Other embodiments of methods for malfunction recognition in a fluid delivery device may include: providing input pulses to rotate a motor in a first direction, monitoring (e.g., using a sensor) the rotation of the motor in the first direction, receiving one or more first sensor signals representative of the rotation of the motor in the first direction, determining a first ratio between a number of input pulses provided to rotate the motor in the first direction and a number of executed motor steps derived from, or otherwise based on, the one or more first sensor signals, determining whether the first ratio exceeds a first threshold, calculating the total number of times it was determined that the first ratio, exceeds the first threshold, determining whether the total number of times it was determined that the first ratio exceeds the first threshold exceeds a second threshold, providing input pulses to rotate a motor in a second direction substantially opposite the first direction upon determining that the total number of times it was determined that the first ratio exceeds the first threshold exceeds the second threshold, receiving one or more second sensor signals representative of the rotation of the motor in the second direction, determining a second ratio between a number of input pulses provided to rotate the motor in the second direction and a number of executed motor steps derived from, or otherwise based on, the one or more second sensor signals, determining whether the second ratio exceeds a third threshold, calculating the total number of times it was determined that the second ratio exceeds the third threshold, determining whether the total number of times it was determined that the second ratio exceeds the third threshold exceeds a fourth threshold, providing one of: an occlusion notification upon determining that the total number of times it was determined that the second ratio exceeds the third threshold does not exceed the fourth threshold, and a device malfunction notification upon determining that the total number of times it was determined that the second ratio exceeds the third threshold exceeds the fourth threshold.

Embodiments of the method may include one or more of the above-described features of the devices and/or of the methods, as well as any of the following features noted below.

In some embodiments, a system for problem determination in a fluid delivery device is disclosed. The system includes a sensor configured to monitor at least one parameter associated with operation of the fluid delivery device, and a controller. The controller is configured to activate a motor of the fluid delivery device, detect an occurrence of a problem in fluid delivery based on one or more first sensor signals generated by the sensor when the motor is activated in a first direction, where the one or more first sensor signals representative of the at least one parameter monitored when the motor is activated in the first direction. The controller is further configured to determine a type of the detected problem based on one or more second sensor signals generated by the sensor when the motor is activated in a second direction substantially opposite the first direction, the one or more second sensor signals representative of the at least one parameter monitored when the motor is activated in the second direction.

Embodiments of the system may include one or more of the above-described features of the devices and/or of the methods, as well as any of the following features noted below.

The controller may be configured to determine whether the one or more first sensor signals correlate with one or more first activation signals provided by the controller to activate the motor in the first direction, to detect the occurrence of the problem.

The controller may be configured to determine whether the one or more second sensor signals correlate with one or more second activation signals provided by the controller to activate the motor in the second direction, to determine the type of the problem.

For detecting the occurrence of the problem, the controller may be configured to determine a first ratio between a first value associated with activation of the motor in the first direction and a second value based on the one or more first sensor signals, and compare the first ratio to a first threshold.

For determining the type of the problem, the controller may be configured to determine a second ratio between a third value associated with activation of the motor in the second direction and a fourth value based on the one or more second sensor signals, and compare the second ratio to a second threshold.

In comparing the first ratio to the first threshold, the controller may be configured to determine whether the first ratio exceeds the first threshold.

The controller, in detecting the occurrence of the problem, may be further configured to calculate a total number of occurrences that determined first ratios exceed the first threshold.

The controller, in detecting the occurrence of the problem, may be further configured to determine whether the calculated total number of occurrences that the determined first ratios exceed the first threshold exceeds a third threshold.

The controller, in detecting the occurrence of the problem, may be further configured to calculate a total number of occurrences that the determined first ratios do not exceed the first threshold, determine a third ratio between the total number of occurrences that the determined first ratios exceed the first threshold and the total number of occurrences that the determined first ratios do not exceed the first threshold, and compare the third ratio to a fourth threshold.

The controller, in comparing the second ratio to the second threshold, may be further configured to determine whether the second ratio exceeds the second threshold.

The controller, in determining the type of the detected problem, may be further configured to calculate a total number of occurrences that determined second ratios exceed the second threshold.

The controller, in determining the type of the detected problem, may be further configured to determine whether the total number of occurrences that the determined second ratios exceed the second threshold exceeds a fifth threshold.

The controller, in determining the type of the detected problem, may be further configured to calculate a total number of occurrences that the determined second ratios do not exceed the second threshold, determine a fourth ratio between the total number of occurrences that the determined second ratios exceed the second threshold and the total number of occurrences that the determined second ratios do not exceed the second threshold, and compare the fourth ratio to a sixth threshold.

In some embodiments, the at least one parameter monitored by the sensor may be rotation of at least one of the motor and one or more gears.

In some embodiments, the at least one of the first value and the second value may correspond to a number of motor rotations, the number of motor rotations being an integer or a non-integer number greater than or equal to 0.

In some embodiments, the first value may correspond to an expected number of motor rotations and the second value corresponds to a number of executed motor rotations.

In some embodiments, the at least one of the third value and the fourth value may correspond to a number of motor rotations, the number of motor rotations being an integer or a non-integer number greater than or equal to 0.

In some embodiments, the third value may correspond to an expected number of motor rotations and the fourth value corresponds to a number of executed motor rotations.

In some embodiments, at least one of the first value and the second value may correspond to a level of power supplied to the motor.

In some embodiments, at least one of the third value and the fourth value may correspond to a level of power supplied to the motor.

In some embodiments, the determined type of the problem may include one of, for example, an occlusion in a delivery line of the fluid delivery device, and a device malfunction.

In some embodiments, the controller configured to determine the type of the problem may further be configured to calculate a total number of occlusion occurrences, determine whether the total number of occlusion occurrences exceeds a threshold, and determine that a device malfunction has occurred upon determining that the total number of occlusion occurrences exceeds the threshold.

In some embodiments, the device malfunction may be a driving mechanism malfunction.

In some embodiments, the controller may further be configured to identify a malfunctioning component associated with the device malfunction.

In some embodiments, the motor may be a stepper motor.

In some embodiments, the controller may further be configured to provide at least one notification to the user corresponding to one or more of the detection of the occurrence of the problem and the determined type of detected problem. The notification may be provided using a remote control in communication with the controller.

In some embodiments, the sensor may include a light source configured to emit light, a light detector configured to detect the light emitted by the light source, and an element coupled to a shaft of the motor and configured to periodically prevent the light detector from detecting the light emitted by the light source by blocking the emitted light.

In some embodiments, a system for problem determination in a fluid delivery device is disclosed. The system includes a sensor configured to monitor at least one parameter associated with operation of a fluid delivery device, and a controller. The controller is configured to activate a motor in a first direction, activate the motor in a second direction substantially opposite the first direction, receive one or more first sensor signals generated by the sensor when the motor is activated in the first direction, the one or more first sensor signals representative of the at least one parameter monitored when the motor is activated in the first direction, and receive one or more second sensor signals generated by the sensor when the motor is activated in the second direction, the one or more second sensor signals representative of the at least one parameter monitored when the motor is activated in the second direction. The controller is further configured to determine a first ratio between a first value associated with the activation of the motor in the first direction and a second value based on the one or more first sensor signals, compare the first ratio to a first threshold, detect an occurrence of a problem in fluid delivery based on the comparison between the first ratio to the first threshold, determine a second ratio between a third value associated with the activation of the motor in the second direction and a fourth value based on the one or more second sensor signals, compare the second ratio to a second threshold, and determine a type of the detected problem based, at least in part, on the comparison between the second ratio to the second threshold.

Embodiments of the system may include one or more of the above-described features of the devices, of the methods and/or of the first system, as well as any of the features noted below.

In some embodiments, a method for problem determination in a fluid delivery device is disclosed. The method includes monitoring at least one parameter associated with operation of the fluid delivery device, activating a motor of the fluid delivery device, detecting an occurrence of a problem in fluid delivery based on one or more first sensor signals generated when the motor is activated in a first direction, the one or more first sensor signals representative of the at least one parameter monitored when the motor is activated in the first direction, and determining a type of the detected problem based on one or more second sensor signals generated when the motor is activated in a second direction substantially opposite than the first direction, the one or more second sensor signals representative of the at least one parameter monitored when the motor is activated in the second direction.

Embodiments of the method may include one or more of the above-described features of the devices, of the methods and/or of the systems, as well as any of the following features noted below.

Detecting the occurrence of the problem in fluid delivery may include determining whether the one or more first sensor signals correlate with one or more first activation signals provided to activate the motor in the first direction.

Determining the type of the detected problem may include determining whether the one or more second sensor signals correlate with one or more second activation signals provided to activate the motor in the second direction.

Detecting the occurrence of the problem in fluid delivery may include determining a first ratio between a first value associated with activation of the motor in the first direction and a second value based on the one or more first sensor signals, and comparing the first ratio to a first threshold.

Determining the type of the detected problem may include determining a second ratio between a third value associated with activation of the motor in the second direction and a fourth value based on the one or more second sensor signals, and comparing the second ratio to a second threshold.

Comparing the first ratio to the first threshold may include determining whether the first ratio exceeds the first threshold.

Detecting the occurrence of the problem may further include calculating a total number of occurrences that determined first ratios exceed the first threshold.

Detecting the occurrence of the problem may further include determining whether the calculated total number of occurrences that the determined first ratios exceed the first threshold exceeds a third threshold.

Detecting the occurrence of the problem may further include calculating a total number of occurrences that the determined first ratios do not exceed the first threshold, determining a third ratio between the total number of occurrences that the determined first ratios exceed the first threshold and the total number of occurrences that the determined first ratios do not exceed the first threshold, and comparing the third ratio to a fourth threshold.

Comparing the second ratio to the second threshold may include determining whether the second ratio exceeds the second threshold.

Determining the type of the detected problem may further include calculating a total number of occurrences that determined second ratios exceed the second threshold.

Determining the type of the detected problem may further include determining whether the total number of occurrences that the determined second ratios exceed the second threshold exceeds a fifth threshold.

Determining the type of the detected problem may further include calculating a total number of occurrences that the determined second ratios do not exceed the second threshold, determining a fourth ratio between the total number of occurrences that the determined second ratios exceed the second threshold and the total number of occurrences that the determined second ratios do not exceed the second threshold, and comparing the fourth ratio to a sixth threshold.

At least one of the first value and the second value may correspond to a level of power consumed by the motor.

At least one of the third value and the fourth value may correspond to a level of power consumed by the motor.

Determining the type of the problem may further include calculating a total number of occlusion occurrences, determining whether the total number of occlusion occurrences exceeds a threshold, and determining that a device malfunction has occurred upon determining that the total number of occlusion occurrences exceeds the threshold.

The method may further include identifying a malfunctioning component associated with the device malfunction.

The method may further include providing at least one notification to the user corresponding to one or more of the detection of the occurrence of the problem and the determined type of detected problem.

The notification may be provided using a remote control in communication with the controller.

Monitoring the at least one parameter may include emitting light, detecting the emitted light, and periodically preventing the detection of the emitted light by blocking the emitted light.

In some embodiments, a method for problem determination in a fluid delivery device is disclosed. The method includes monitoring at least one parameter associated with operation of a fluid delivery device, activating a motor in a first direction, receiving one or more first sensor signals generated when the motor is activated in the first direction, the one or more first sensor signals representative of the at least one parameter monitored when the motor is activated in the first direction, determining a first ratio between a first value associated with the activation of the motor in the first direction and a second value based on the one or more first sensor signals, and comparing the first ratio to a first threshold. The method further includes detecting an occurrence of a problem in fluid delivery based on the comparison between the first ratio to the first threshold, activating the motor in a second direction substantially opposite the first direction upon detecting the occurrence of the problem, receiving one or more second sensor signals generated by the sensor when the motor is activated in the second direction, the one or more second sensor signals representative of the at least one parameter monitored when the motor is activated in the second direction, determining a second ratio between a third value associated with the activation of the motor in the second direction and a fourth value based on the one or more second sensor signals, comparing the second ratio to a second threshold, and determining a type of the detected problem based, at least in part, on the comparison between the second ratio to the second threshold.

Embodiments of the method may include one or more of the above-described features of the devices, of the systems and/or of the methods, as well as any of the following features noted below.

Determining the type of the detected problem may include distinguishing between an occlusion in a delivery line of the fluid delivery device and a malfunctioning component of the fluid delivery device.

The method may further include identifying the malfunctioning component upon determining that the detected problem is a malfunction in a component of the fluid delivery device.

Embodiments of the devices, systems and methods disclosed above may include one or more of the above-described features of any of the disclosed devices, systems and/or methods.

Details of one or more implementations are set forth in the accompanying drawings and in the description below. Further features, aspects, and advantages will become apparent from the description, the drawings, and the claims.

BRIEF DESCRIPTION OF THE DRAWINGS

Some of the embodiments of the present disclosure are described with reference to the accompanying drawings. In the drawings, like reference numbers indicate identical or functionally similar elements.

DETAILED DESCRIPTION

Figure 1:
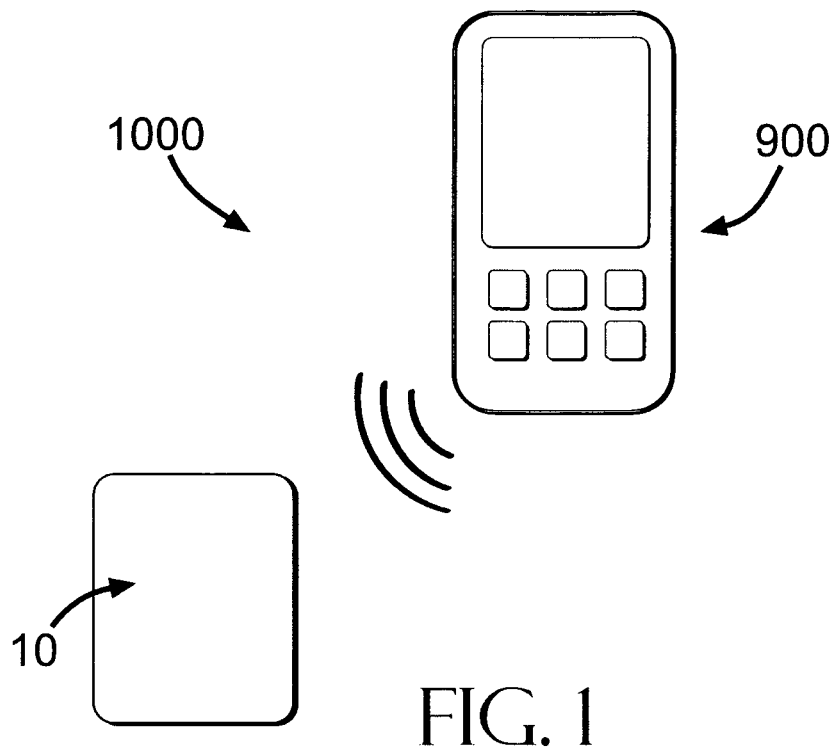
FIG. 1 illustrates an example fluid delivery system that includes a dispensing device/unit and a remote control device/unit, according to some embodiments.

FIG. 1 illustrates an example system, according to some embodiments, which includes a fluid delivery system 1000 for infusion of therapeutic, fluid(s) into a body of a patient/ user. The system 1000 may include a dispensing unit 10 and a remote control unit 900 ("remote control"). In some embodiments, the dispensing unit 10 may be referred to as a "patch unit" due to its structural similarity to a thin patch that can be affixed/secured to the patient's body. The dispensing unit 10 may be adherable to the skin of the patient. In some embodiments, the fluid delivery system 1000 may further include a cradle unit (not shown) for securing the dispensing unit 10 to the body of the patient. In some embodiments, the remote control 900 may be configured as a handheld device for programming fluid infusion rates, controlling the dispensing unit, acquiring data, and providing visual, audible and/or vibratory notifications. In some embodiments, the remote control may be configured, without limitation, as a wristwatch, a cellular phone, a personal digital assistance, iPhone, iPod, an mp3 player or a personal computer. In some embodiments, the system 1000 does not include a remote control 900 and the dispensing unit 10 may be operated using a user interface (e.g., a button-based interface) provided on a housing of the dispensing unit 10, as disclosed, for example, in co-owned International Patent Applications Publication Nos. WO/2009/013736 and WO/2009/016636, the contents of all of which are hereby incorporated by reference in their entireties. Embodiments of the cradle unit ("cradle") may be configured as a substantially flat sheet or plate including a surface that can be secured (e.g., adherable) to the patient's skin, e.g., via an adhesive layer provided on a bottom surface of the cradle. The cradle may also contain a passageway for insertion of a cannula into the body. Embodiments of a system comprising a cradle are disclosed, for example, in co-owned, co-pending U.S. Patent Application Publication No. 2008-0215035 and in co-owned International Patent Application Publication No. WO/2008/078318.

In some embodiments, the dispensing unit (e.g., insulin pump) may further include an analyte (e.g., glucose) sensor providing an open and/or closed loop system. Examples of such a device are disclosed, for example, in co-owned U.S. Patent Applications Publication Nos. 2007-0191702 and 2008-0214916, and International Patent Applications Publication Nos. WO/2007/093981 and WO/2008/078319, the disclosures of all of which are incorporated herein by reference in their entireties.

Figure 2A:
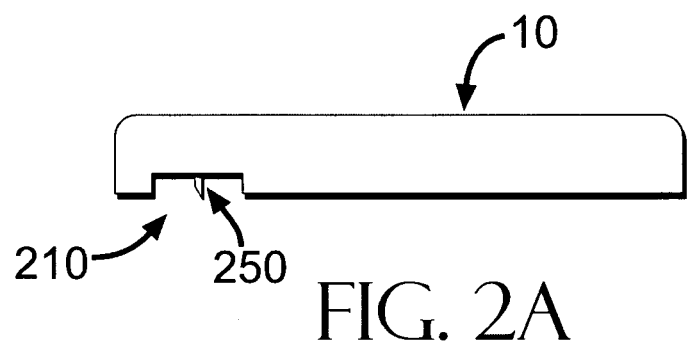
FIGS. 2A-2B illustrate an example fluid delivery device which includes a dispensing unit that can be composed of one part (FIG. 2A) or two-parts (FIG. 2B), according to some embodiments.
Figure 2B:
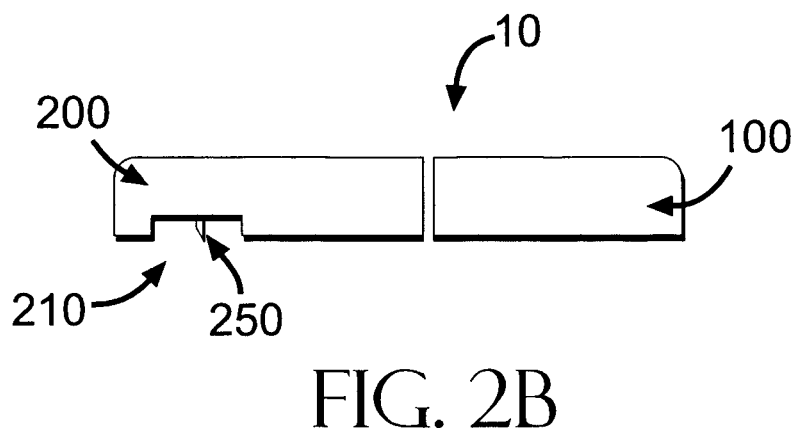

FIGS. 2A-2B illustrate embodiments of the dispensing unit 10. The dispensing unit 10 may include an outlet port 210 provided with a connecting lumen 250 configured to enable fluid communication between a reservoir (located in the dispensing unit 10, for example) and the patient's body, via a subcutaneously inserted cannula, for example. The dispensing unit 10 may include a single part (FIG. 2A), or, in some embodiments, two parts (FIG. 2B). The two-part dispensing unit 10 may include a reusable part 100 and a disposable part 200. The reusable part 100 may include the driving mechanism (not shown), or at least a portion of the driving mechanism (e.g., motor, one or more gears), and the disposable part 200 may include the reservoir (not shown). In some embodiments, the disposable part 200 may also include a portion of the driving mechanism (e.g., nut, drive screw). The disposable part 200 may include the outlet port 210 with the connecting lumen 250. A two-part dispensing unit is disclosed, for example, in co-owned, co-pending U.S. Patent Application Publication No. 2007-0106218, and in co-owned International Patent Application Publication No. WO/2007/052277, the contents of all of which are incorporated herein by reference in their entireties.

Figure 3A:
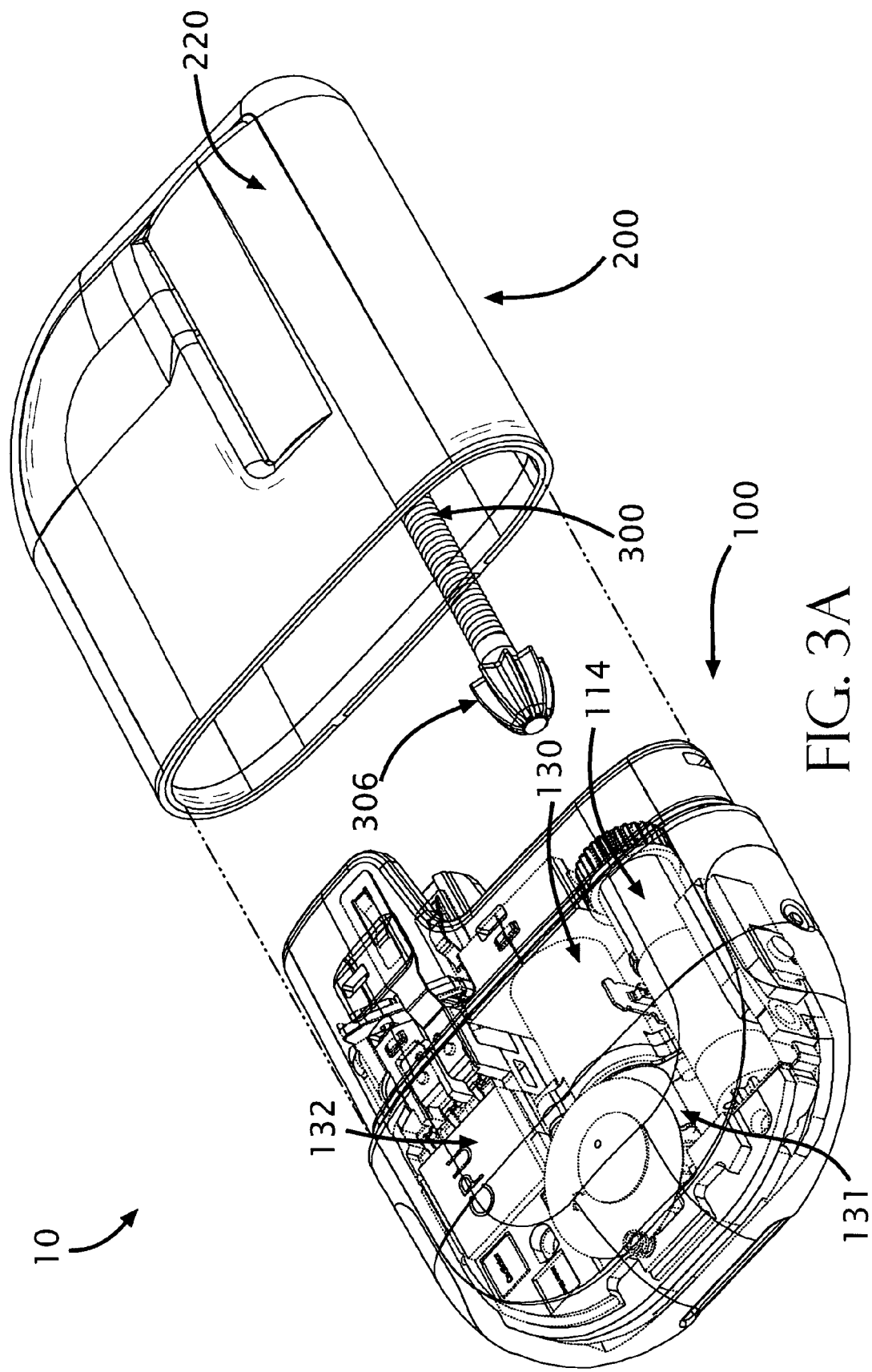
FIG. 3A is a diagram of a two-part dispensing unit including a reusable part that includes a controller, a motor and a gear box, and a disposable part that includes a reservoir and a drive screw, according to some embodiments.

FIG. 3A shows an embodiment of a patch unit 10 having two parts—a reusable part 100 and a disposable part 200. The pumping mechanism of the patch unit 10 may be, for example, a piston-type pump (e.g., a syringe-like mechanism) that includes a plunger (not shown) within a reservoir 220. Other types of pumping mechanisms may be used. The reusable part 100 may include relatively expensive components, including, without limitation, a motor 131, one or more gears 130 (e.g., a gear box), a rotating sleeve 114, and/or electronic components including one or more controllers/ processors (e.g., CPU, MCU) 132. The motor 131 may be, without limitation, a DC motor, a stepper motor, or a shape memory alloy motor, and the one or more gears 130 may include, without limitations, external gears, internal gears, spur gears, helical gears, bevel gears or any combination thereof. In some embodiments, the one or more gears 130 may be arranged in the form of a planetary gear system. The disposable part 200 may include a reservoir 220, a plunger (not shown), a plunger rod that may be configured as a threaded drive screw 300 having a distal end (not shown) to engage with the plunger and a proximal engagement end 306 for engagement with the rotating sleeve 114 or with any other receiving component located in the reusable part 100 and configured for engagement with the proximal end 306. Some embodiments may include a power source (e.g., one or more batteries), which may be located in the disposable part 200. In some embodiments, the power source may be located in the reusable part 100. In some embodiments, the power source may be located partially in both the disposable part 200 and the reusable part 100 when the two parts are connected. An example of the device shown in FIG. 3A is disclosed, for example, in International Patent Application Publication No. WO/2009/125398, filed on Apr. 7, 2009, the disclosure of which is incorporated herein in its entirety.

Figure 3B:
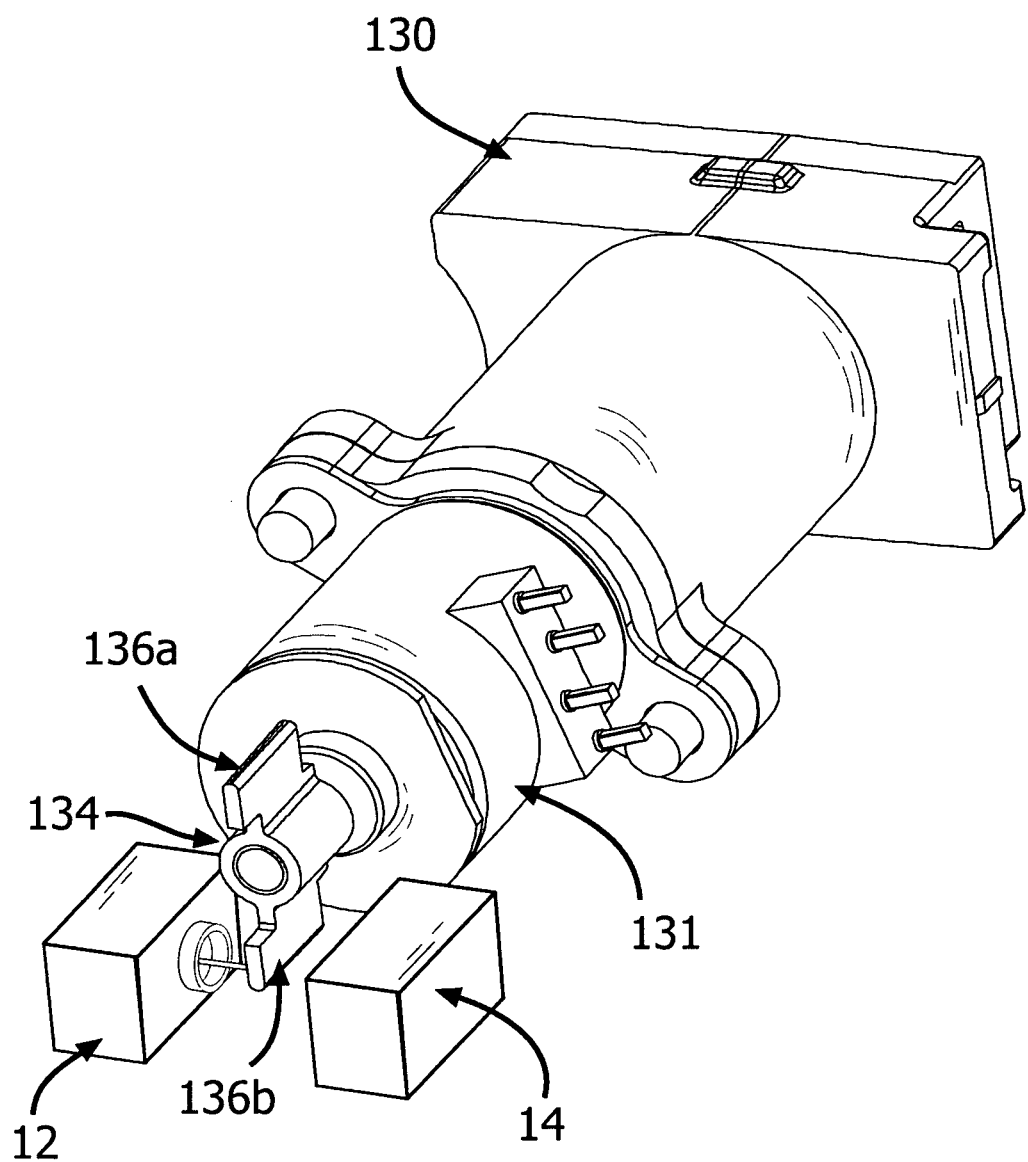
FIG. 3B is a diagram of a motor, a gear box, and a sensor for monitoring the motor's rotation, according to some embodiments.

FIG. 3B shows an exemplary driving mechanism including a motor 131 and a gear box 130, and an embodiment of a sensor (e.g., an encoder) monitoring the rotation of the motor 131. In some embodiments, the motor 131 is operatively coupled to the gear box 130 at one end and an "encoder propeller" 134, which may include one or more fins, e.g., two fins 136a and 136b, is attached to the other end of the motor shaft. Depending on the embodiment, the encoder propeller 134 may be attached to another component of the driving mechanism, as disclosed, for example, in co-owned International Patent Application Publication No. WO/2008/139459. In some embodiments, a LED 12 may be aligned with a phototransistor 14, such that each is positioned on a different side of the encoder propeller 134, opposite each other. During motor rotation, the encoder fins 136a and 136b periodically block the light emitted from the LED 12 toward the phototransistor 14. The phototransistor 14 produces signals according to the light intensity applied to it. Thus, the signals generated by the phototransistor 14 correspond to the rotation of the motor shaft. In some embodiments, the phototransistor signals enable determination of the number of rotations executed by the motor 131 and the consequent movement of the driving mechanism. The number of fins determines the resolution of the monitoring, e.g., if the encoder propeller 134 includes one fin (e.g., fin 136a), the phototransistor signals may indicate completion of full motor rotations, whereas if the encoder propeller 134 includes two or more fins (e.g., fins 136a and 136b), the phototransistor signals may indicate completion of portions (e.g., half) of a motor rotation.

Figure 4:
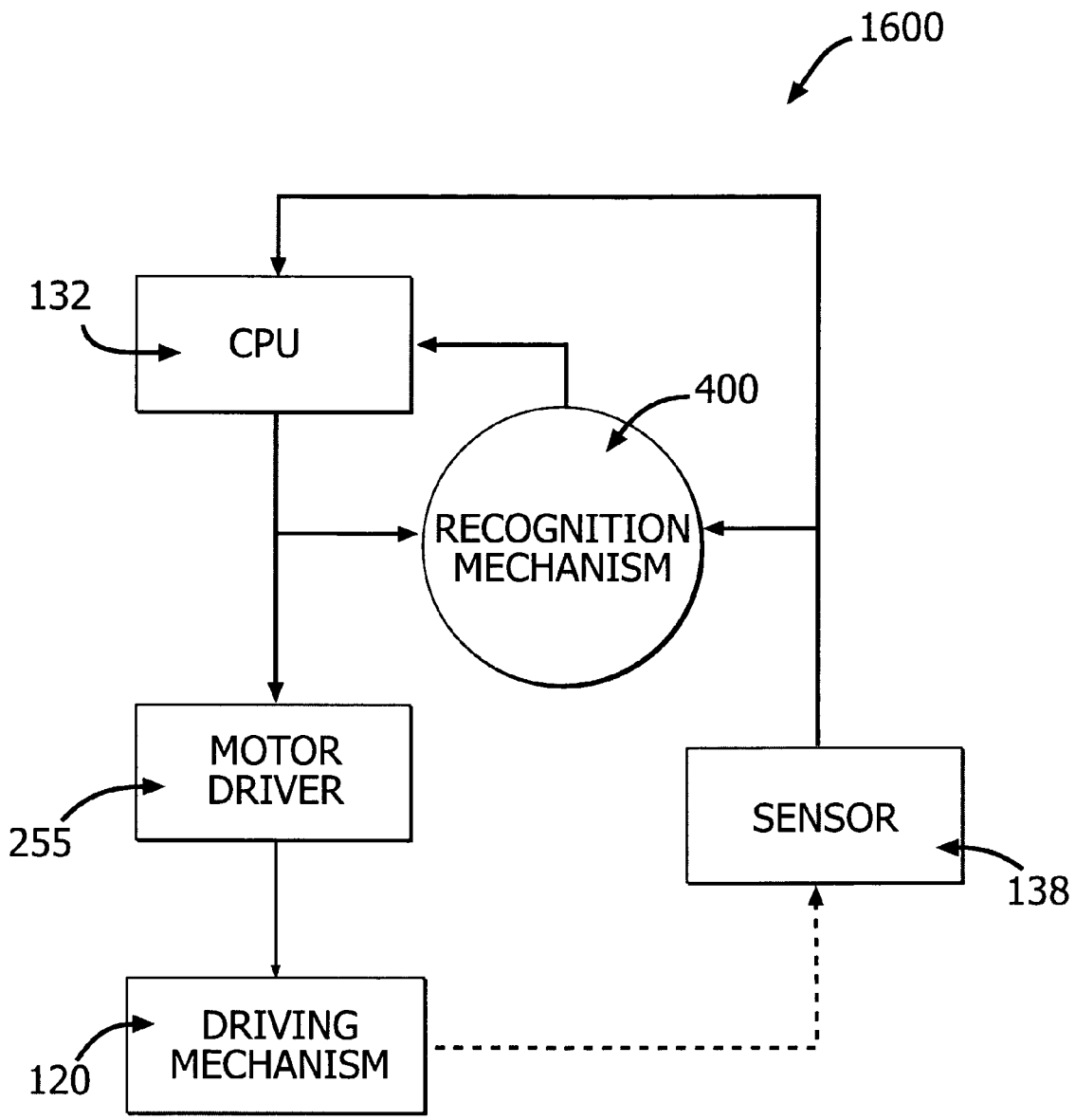
FIG. 4 is a block diagram depicting a motor activation and error detection feedback procedure, according to some embodiments.

FIG. 4 shows a block diagram of an error recognition feedback system 1600, according to some embodiments. The system 1600 may include:

A controller (e.g., CPU) 132 to control and monitor at least some of the fluid delivery device operations, such as controlling the amount of therapeutic fluid to deliver, controlling the motor's operation, analyzing signals generated by sensors, e.g., sensor 138, etc.

A driving mechanism 120, which may include a motor (e.g., a stepper motor, a DC motor, a SMA actuator) and at least one gear.

A motor driver 255 to provide power to the motor from a power supply (e.g., a battery). In some embodiments, pulsed power is provided to the motor, e.g., the power is accumulated in a capacitor and released in a short burst.

A sensor or monitor 138 for monitoring the operation of the fluid delivery device. The sensor 138 may be configured to monitor the driving mechanism's operation (e.g., the rotation of one or more of the driving mechanism's components, monitored, for example, using the encoder shown in FIG. 3B). In some embodiments, a revolution counter may be used as the sensor 138. Such a revolution counter is disclosed, for example, in co-owned International Patent Application Publication No. WO/2008/139459, the disclosure of which is incorporated herein by reference in its entirety. In some embodiments, the sensor 138 may be configured to monitor one or more parameters that are associated with fluid delivery and are affected by the driving mechanism's operation. Such parameters may include, without limitations, therapeutic fluid flow rate, therapeutic fluid temperature, plunger position within the reservoir, internal pressure of the tubing/reservoir, force required to move the plunger and torque of the motor. Accordingly, the sensor 138 may be coupled to the driving mechanism (e.g., to the motor, as shown in FIG. 3B), and/or to any other component of the device, depending on the monitoring mechanism. In some embodiments, the sensor 138 may include at least one of the following: LED and phototransistor, a Hall effect sensor, a current sensor, a voltage sensor and an ADC (analog to digital converter).

An error recognition mechanism 400, e.g., implemented by, for example, software executed by the controller 132, for detecting occlusion or device malfunctions, such as driving mechanism malfunctions. In some embodiments, the error recognition mechanism 400 receives signals from the sensor 138 indicating the number of rotations (or fractional rotations) completed by the shaft of the motor. The number of motor rotations (or fractional rotations) may then be compared to the power provided to the motor by the motor driver 255 and/or controller 132, for example. If the two parameters correlate (e.g., their ratio is in some predetermined range), then no error/problem is deemed to have been detected. If the two parameters do not correlate (e.g., their ratio is outside some predetermined range), then an error/problem is deemed to have been detected. In case a stepper motor is employed, for example, the compared parameters may be pulses sent to the motor and steps executed by the motor.

In some embodiments, the error recognition mechanism 400 implements a process to distinguish an occlusion related error from other types of errors (e.g., motor malfunctions, deformations in the driving mechanism, faulty encoder). For example, upon error detection (e.g., if the ratio of the two determined parameters are outside a pre-determined range), the motor may, for example, be rotated in reverse (the shaft is rotated in the opposite direction), and once again the rotation of the shaft of the motor and the power provided to the motor are compared. If during the motor's reverse rotation no error is detected, indicating that the error occurs only during therapeutic fluid delivery (i.e., forward rotation of the motor), then the error is determined to be an occlusion. Otherwise, i.e., if an error is detected in both forward and backward rotation of the motor, the error is recognized as a device malfunction (e.g., a motor error). Using a single monitoring instrument (e.g., sensor 138) to determine the occurrence of both an occlusion condition and device malfunction reduces the overall cost of the device and may also reduce the overall size of the device, as there is no need for an additional space-occupying sensor. Example processes for determining the nature of the error/problem that occurred, e.g., distinguishing an occlusion related problem from other types of problems, are further shown in FIGS. 5 and 7. According to some embodiments, error detection may be performed by an error detection mechanism, whereas error recognition (i.e., determining the nature of the error/problem that occurred to thus enable, for example, to distinguish between an occlusion and a device malfunction) may be performed by another device/unit/mechanism. Alternatively, both error detection and error recognition may be performed by the same mechanism. The error recognition mechanism may be implemented as software code (stored, for example, on non-transitory storage medium) run by the fluid delivery device controller, according to some embodiments, or it may be implemented entirely as a hardware-based mechanism. The controller may control the motor, and thus can compute the power provided to the motor and compare it to signals received from a sensor monitoring the driving mechanism, for example.

Figure 5:
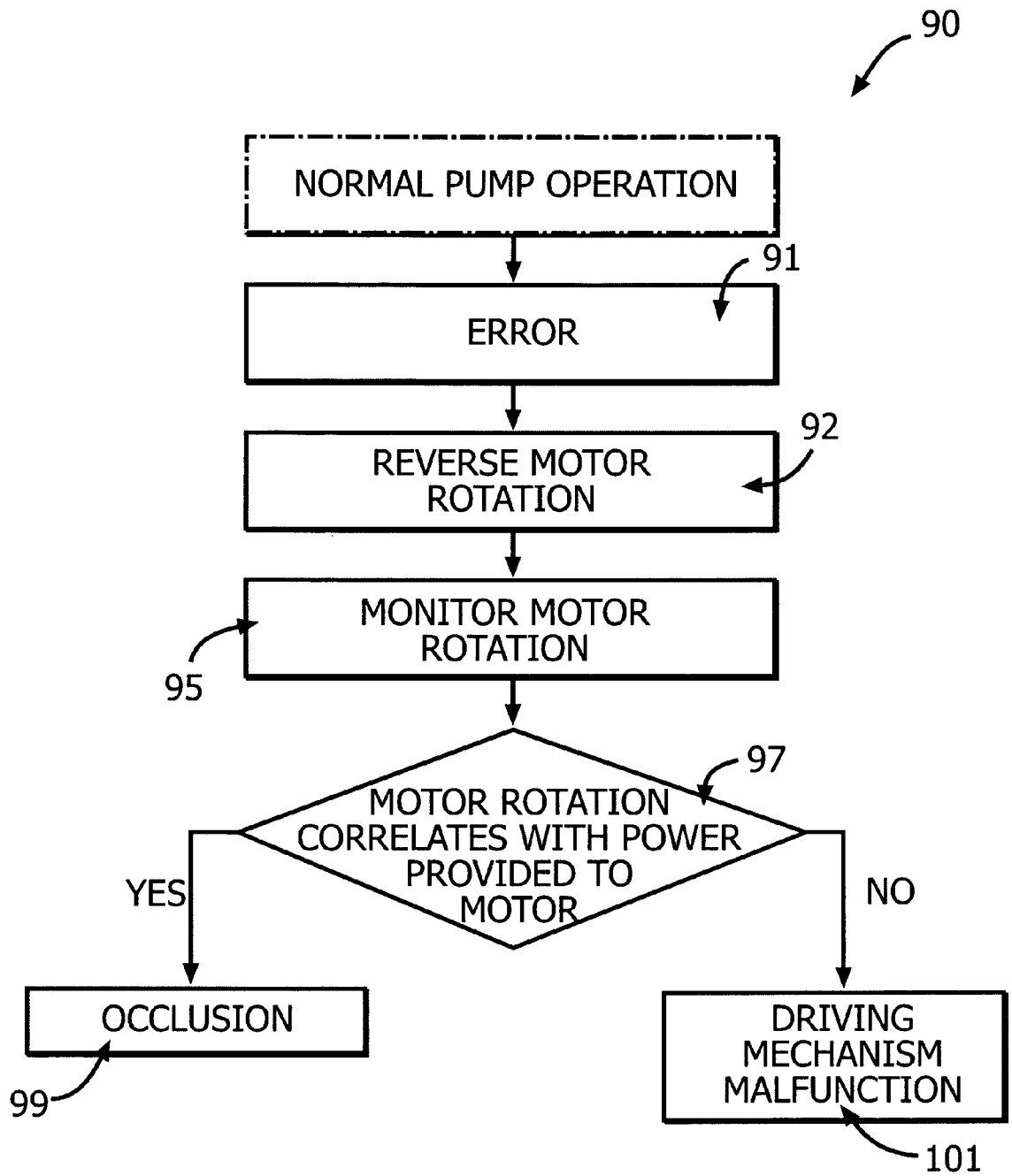
FIG. 5 is a flowchart of an example process for errors detection and errors classification, according to some embodiments.
Figure 7:
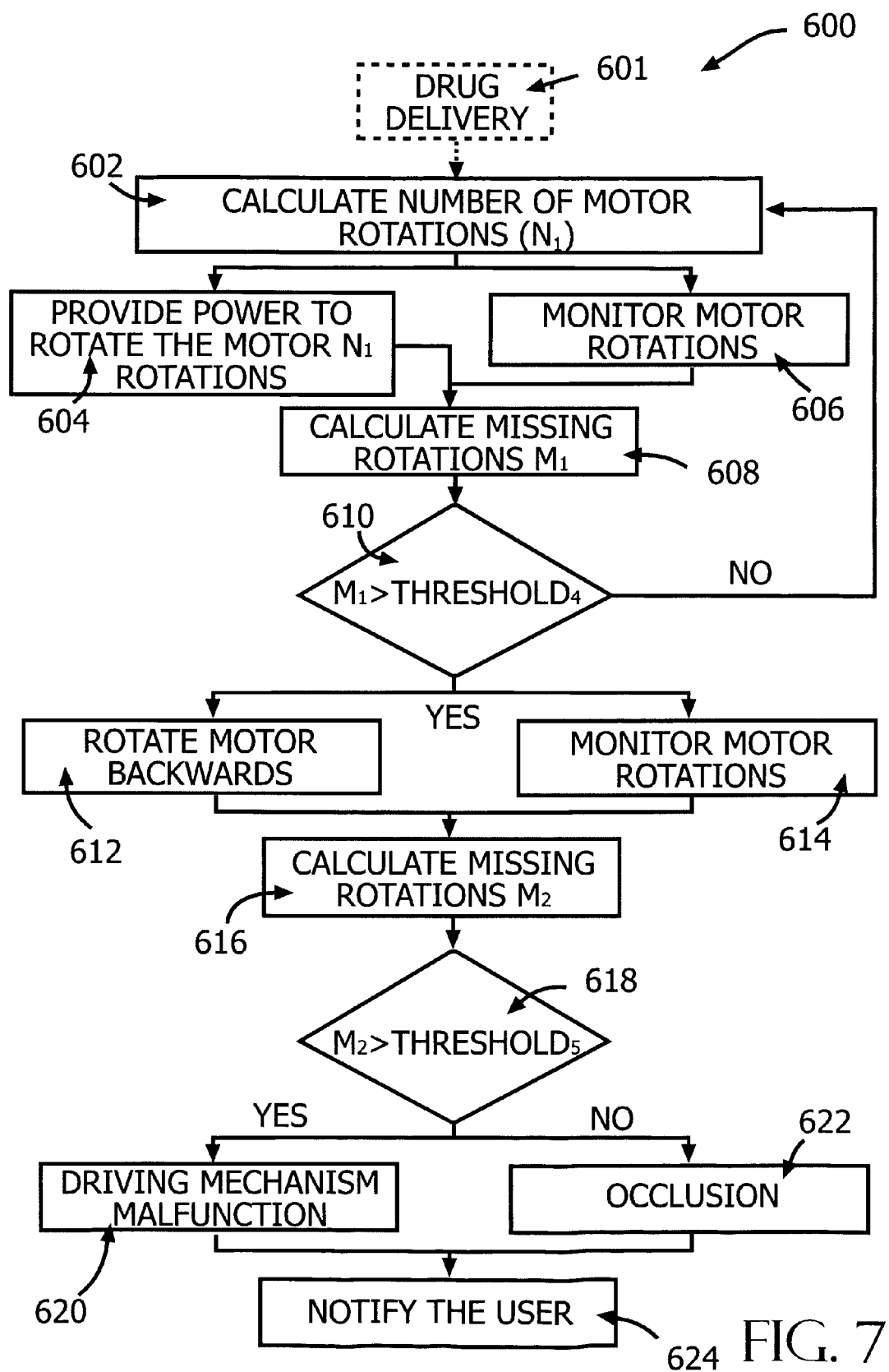
FIG. 7 is a flowchart of an example process for errors detection and errors classification based on motor rotation, according to some embodiments.
Figure 8:
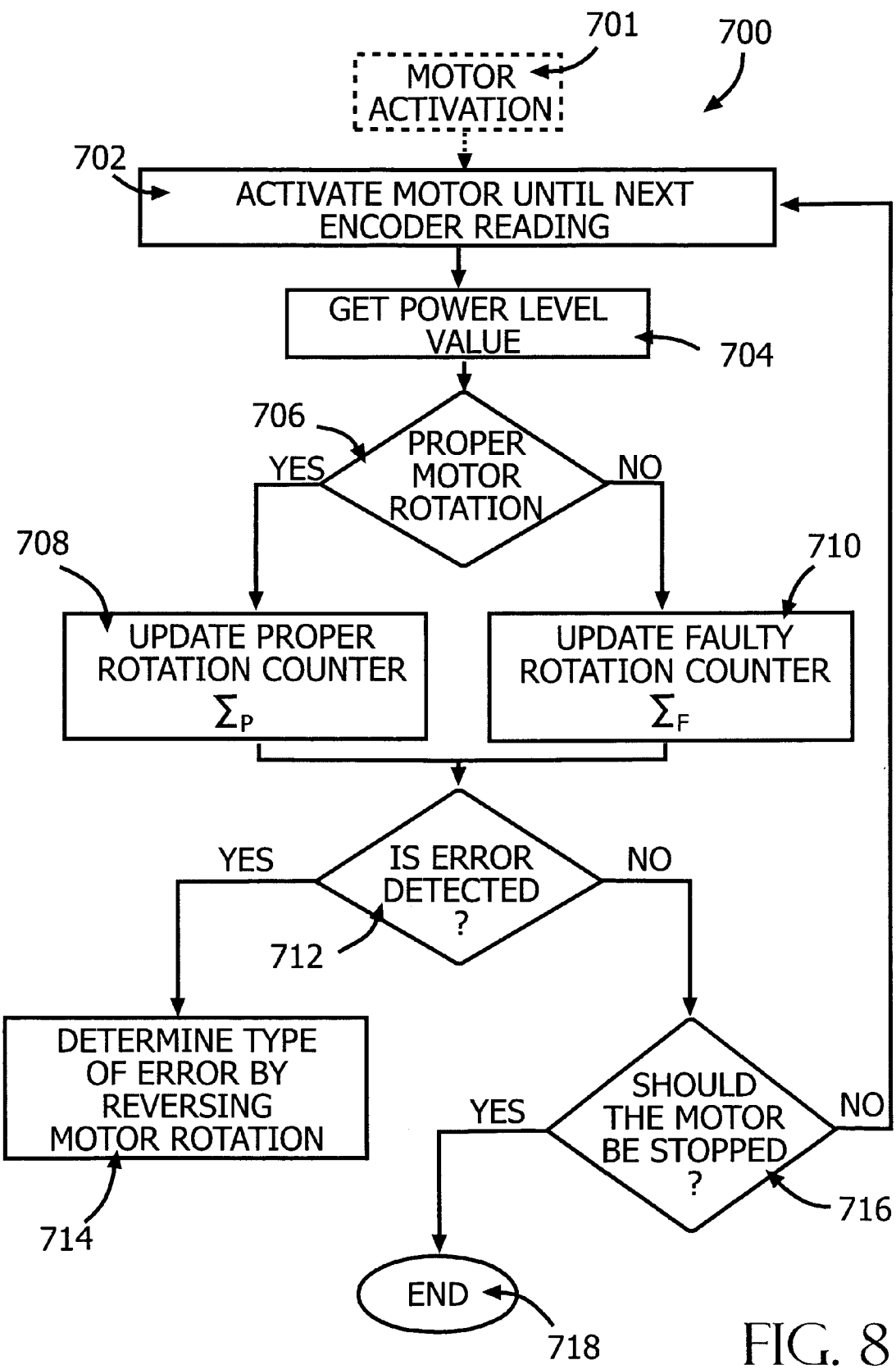
FIG. 8 is a flowchart of an example process for errors detection and errors classification based on the number of faulty/proper motor rotations, according to some embodiments.

FIG. 5 shows a flowchart of an example, error recognition procedure 90. This procedure may be implemented, for example, using the therapeutic fluid dispensing device controller. According to some embodiments, the procedure is activated after an error/problem is detected during device operation. An error may be detected by monitoring at least one parameter related to the therapeutic fluid delivery (e.g., pressure in the reservoir, therapeutic fluid flow) and/or comparing at least two parameters related to the therapeutic fluid delivery, such as parameters associated with the driving mechanism (e.g., power supplied to the motor and encoder reading). In some embodiments, an error may be determined to have occurred each time a threshold is reached (e.g., a threshold relating to a value of a specific parameter, or a threshold relating to the relationship between two or more parameters). In some embodiments, an error may be determined to have occurred after a threshold has been reached a certain number of times (e.g., an absolute number of times, a certain number of times within a predetermined time period, or a certain number of times within a predetermined number of motor cycles/activations). In some embodiments, the threshold may be pre-programmed (e.g., as a fixed value, or as a fixed percentage). In some embodiments, the threshold may be established during normal operation of the device, e.g., during priming of the device. In case a two-part dispensing unit is employed, as shown for example in FIGS. 2B and 3A, the threshold may be determined anew after, for example, each disposable part replacement. Example error detection procedures are shown in FIGS. 7 and 8, for example.

As shown in FIG. 5, upon error detection 91, which occurs during the driving mechanism operation, according to some embodiments, the direction of rotation of the motor is inverted/reversed 92. When the motor is activated in the reverse direction (i.e., backwards), no therapeutic fluid is delivered to the user's body. During the reverse rotation, the motor's rotation is monitored 95, e.g., by an encoder.

After rotating the motor backwards 92 and monitoring its rotation 95, the power provided to the motor is compared 97 with the monitored degree of rotation (e.g., with the number of completed rotations/fractional rotations) to determine if an occlusion has occurred or if the error is related to a device malfunction (e.g., a malfunction in a driving mechanism component). In some embodiments, the parameters compared may be the number of expected motor rotations/fractional rotations (i.e., given the power provided to the motor) and the number of rotations/fractional rotations completed by the motor. In case a stepper motor is employed, the parameters compared may be pulses sent to the motor and steps executed by the motor. If the two parameters correlate (e.g., the ratio between them is within a predetermined acceptance range, as determined, for example, during the comparing operation 97), indicating that most of the electrical power provided was transformed to mechanical work, no device malfunction (e.g., driving mechanism malfunction) has been found and it is therefore determined 99 that an occlusion has occurred. If the two parameters do not correlate (e.g., the ratio between them is outside an acceptance range, as determined, for example, during the comparing operation 97), it is determined 101 that a malfunction has occurred in one or more components of the device (e.g., a driving mechanism malfunction), and further processing can be conducted to determine the malfunctioning component. The comparison can be done during and/or after motor activation, and, furthermore, the motor may be activated in intervals wherein the comparison may take place between the intervals.

In some embodiments, the error recognition procedure (e.g., procedure 90) may not include further processing to determine the malfunctioning component, for example, in situations where many types of the possible device malfunctions can be identified and/or repaired only by a technician and/or may require specific equipment.

In some embodiments, the results of the comparison operation (in 97) may be recorded in a memory, to be processed at a later point. The processing may include performing correlation computations for one or more of: validation, finding a trend, and the like. Furthermore, the efficiency of the driving mechanism (e.g., the number of executed motor rotations divided by the motor's power consumption) when no error is detected (e.g., during normal/proper operation of the driving mechanism) can be determined.

In some embodiments, the duration of reverse rotation (in 92) is set to be sufficiently long to ensure that if the detected error is related to a malfunctioning component, the error will be detected during reverse rotation. Thus, the duration of reversed movement may depend on the gear ratio, efficiency, and other parameters. In some embodiments, the duration of reverse rotation may be preset (e.g., a fixed length of time or a fixed number of rotations). In some embodiments, the duration of reverse rotation may be adjustable, e.g., in circumstances where the behavior of the motor leading to the detection of the error provides indication as to a possible malfunctioning component, the duration of reverse rotation may be adjusted according to the estimated time required to detect the specific malfunction. For example, a stuck motor or malfunctioning sensor will typically result in many successive faulty signals and may thus require less time to detect compared to errors resulting from a deformed or misplaced gear, which may function normally from time to time and thus, may require more backwards rotations to detect their malfunction. In some embodiments, the duration of reverse rotation may be adaptive, e.g., it may be adjusted while the motor is being activated in reverse, in case there is an indication early during the reverse rotation that the detected error is related to a device malfunction (i.e., a malfunctioning component), for example.

In some embodiments, the relationship between the power consumption and motor rotations at which an error/problem, is recognized (i.e., the acceptance range/the threshold) can be altered (adjusted) during the device lifetime, e.g., according to the driving mechanism's efficiency. In some embodiments, adjustment of thresholds may be desired if a device's efficiency is expected to vary due to wear of the driving mechanism and change of friction forces (for example). This adjustment may be possible as the efficiency change resulting from wear-and-tear is gradual, whereas when an occlusion or malfunction occurs, the efficiency changes rapidly. Thus, in some embodiments, the allowed ratio between the power consumption and motor rotations can be adjusted during the life of the device, without affecting error detection and/or recognition.

It should be noted that this example procedure (specifically the operations in 95 and 97) corresponds to embodiments in which the motor rotation is monitored by an encoder. Other embodiments of procedure 90 may include other monitoring methods and/or sensors, including, but not limited to, one or more of (or a combination thereof): a force sensor, a pressure sensor, a load cell, a hall effect sensor, a torque meter, a flow meter, and/or a current measurement sensor for the motor. Furthermore, other component characteristics may be monitored, such as, for example, the plunger's position within the reservoir, movement (e.g., rotation) of other components of the driving mechanism (e.g., gears, shaft), etc.

Figure 6:
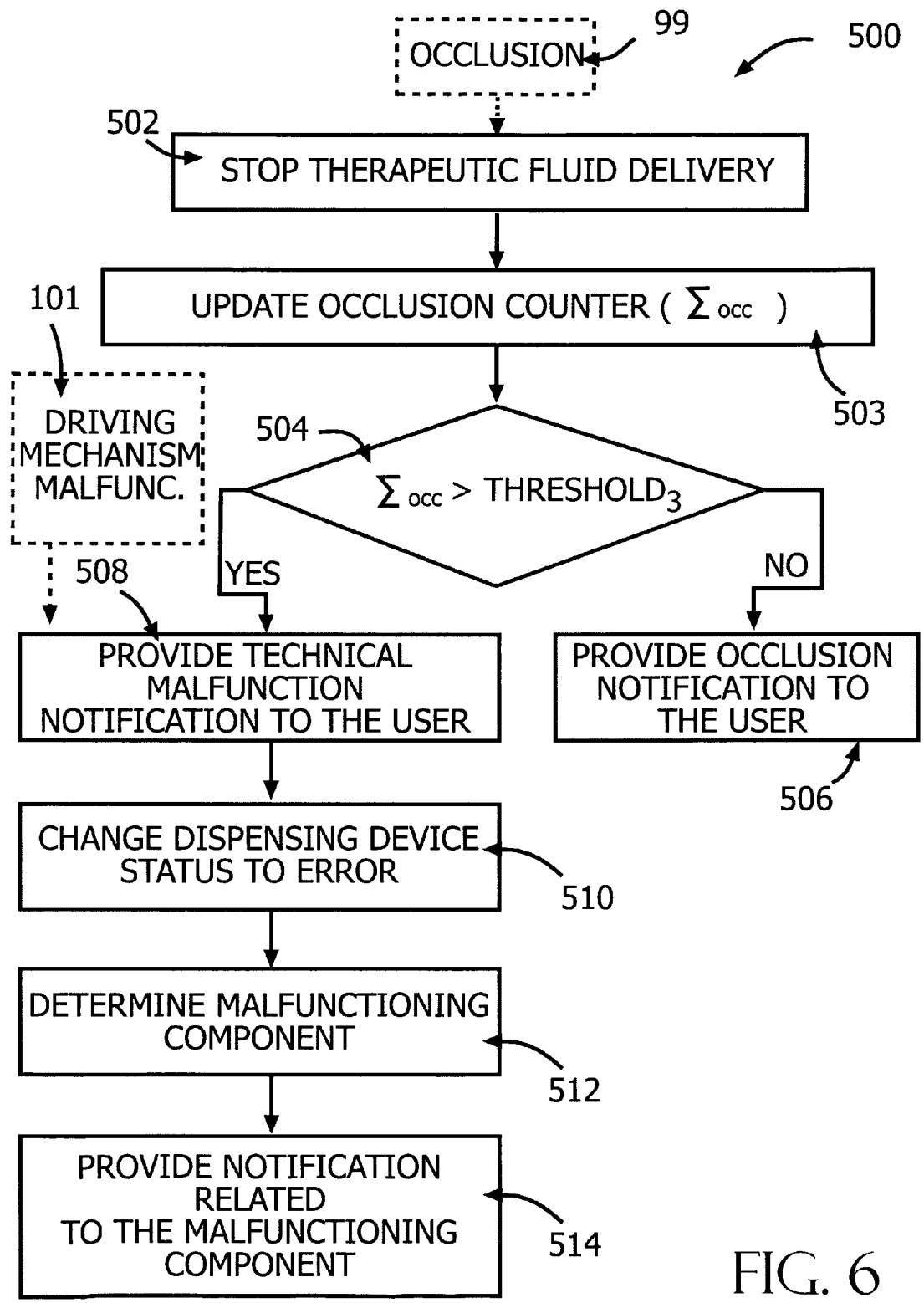
FIG. 6 is a flowchart of an example process for handling occurrence of occlusion and other malfunctions, according to some embodiments.

FIG. 6 shows a flowchart of an example occlusion and device malfunctions handling procedure 500, according to some embodiments. The procedure 500 can be initiated after it has been determined, e.g., via procedure 90 depicted in FIG. 5, that an occlusion and/or a device malfunction (e.g., driving mechanism malfunction) has occurred in a therapeutic fluid dispensing device (or system). Upon commencement of the procedure 500, e.g., following the determination 99 that an occlusion condition exists, the therapeutic fluid delivery to the user's body is stopped 502. According to some embodiments, stopping the therapeutic fluid delivery reduces the risk of a spontaneous occlusion release that may have an effect on the user's health (e.g., hypoglycemia). Afterwards, the occlusion Counter, $\Sigma Occ$, is updated 503. The occlusion counter sums the number of occlusion conditions (or occurrences) in a determined interval. The interval may be a pre-defined time period, e.g., a day, a week, the time between part replacement (e.g., of a reservoir, infusion set, cannula, battery), and the like. In some embodiments, the interval may be based on parameters associated with the operation of the device, e.g., an amount of delivered therapeutic fluid, completed motor cycles, etc. Next, the value of the Occlusion Counter $\Sigma Occ$ may be compared 504 to a threshold (e.g., Thershold$_3$). This threshold may be related to the number of occlusion detections predicted in the determined interval. If $\Sigma Occ$ equals to or is lower than Threshold$_3$, then an occlusion notification is provided to the user 506. The notification may be provided to the user via a remote control display and/or via a user interface (e.g., display) provided on a housing of the dispensing unit. Such notification may further include one or more of, for example: instructions of resolving the occlusion condition (e.g., replacing the cannula), the time of detection and/or the amount of therapeutic fluid delivered until detection of the occlusion (for example). Otherwise, if $\Sigma Occ$ is higher than Threshold$_3$, resulting from occlusion reoccurrence, this may indicate a malfunctioning component. Accordingly, a notification related to the malfunction may be provided to the user 508. In some embodiments, prior to the comparison to Thershold$_3$, the value of the Occlusion Counter $\Sigma Occ$ may be compared to another threshold (e.g., Thershold$_2$), which is lower than Thershold$_3$. If $\Sigma Occ$ equals to or is lower than that Threshold$_2$, then therapeutic fluid delivery may be resumed, either automatically or actively by the user after receiving appropriate instructions via the remote control and/or the display provided on the housing of the dispensing unit. Otherwise, the Occlusion Counter ΣOcc is compared 504 to Thershold₃, as described above.

A malfunctioning component can be also detected by another procedure, e.g., procedure 90 shown in FIG. 5, and may also result in the activation of procedure 500 (at least in part), as a result of the determination 101. With continued reference to FIG. 6, after delivering the notification to the user 508, the therapeutic fluid dispensing device status may be changed 510 to error status. In some embodiments, the status of the device may be changed prior to delivering the notification to the user. The error status may be set in order to limit the usage of the device. For example, only data transfer from, to and/or within the dispensing device may be enabled under this condition. In some embodiments, fluid delivery may be limited in error status as the device malfunction may affect the user's health.

Next, the malfunctioning component may be determined 512, possibly by performing another process, by, for example, checking the integrity of the components. In some embodiments, determining which component is malfunctioning may be done by self-testing. For example, the integrity of software and hardware components can be verified by restarting them. Mechanical malfunctions can be detected by using force or torque measurements to verify proper condition of the components. The motor can be activated back and forth to detect the position in which the error/problem occurred. Electrical and mechanical integrity can be verified by monitoring voltage over electrical components to detect short-circuits, disconnections and/or detachments of electrical components. In some embodiments, the device inspection is conducted with the user's assistance, e.g., the user provides feedback or activates the device in a specific manner. For example, the user may be instructed to disconnect the infusion set from the device and prime it.

After performing inspection operations as part of the determination operations 512, a notification relating to the malfunctioning component may be provided 514. The notification may be provided to the user, a technician and/or to customer service, either directly (e.g., via the device display or a notification component) or indirectly (via interne, phone, etc.). The notification may be audible, visible and/or tactile, and it may be provided by a dispensing unit, another component of the dispensing device (e.g., remote control), or another device (e.g., cellular phone, laptop, PDA).

As there may be many components in the device, including software, hardware (e.g., CPU), electrical (e.g., amplifier operatively connected to the sensor) and mechanical (e.g., gear), the identification of a malfunction in such components might not easily be determined and/or repaired by the user. Thus, step 512 and/or step 514 may be omitted under those circumstances.

FIG. 7 shows a flowchart of an example malfunction detection procedure 600, according to some embodiments. First, the number of required motor rotations N₁ is determined 602. The power required to achieve N₁ motor rotations may also be determined in step 602. In some such embodiments, the number of rotations N₁ is derived from the amount of therapeutic fluid to be delivered into the user's body (e.g., according to a basal/bolus profile set by the user), and thus, it is part of the drug delivery procedure 601. The number of rotations N₁ may refer to full motor rotations and/or to fractional rotations and/or to discrete motor steps (in case a stepper motor is employed, for example). Next, the motor may be activated 604 to accomplish the determined number of rotations N₁ (e.g., N₁ input pulses are provided to the motor to accomplish N₁ discrete motor steps), and its rotation is monitored 606 to determine the actual (i.e., executed) number of rotations. Using N₁, the number of missing rotations M₁ is calculated 608, e.g., by subtracting the actual number of rotations from the expected number of rotations (N₁). It will be noted that the number of missing rotations M₁ may refer to full motor rotations and/or to fractional rotations and/or to discrete motor steps. In some embodiments, the number of required motor rotations N₁ may refer to full motor rotations whereas the number of missing rotations M₁ may refer to discrete motor steps, for example. In such cases, the number of missing steps may be calculated, for example, by subtracting the actual number of rotations from the expected number of rotations and then multiplying the result (i.e., the number of missing rotations) by the number of steps required to complete a single rotation of the motor. Based on the number and/or pattern of missing rotations, errors may be detected. For example, the number of missing rotations may be compared 610 to a threshold (e.g., Thershold₄). If there are more missing rotations than the threshold (i.e., M₁>Thershold₄), an error/problem is determined to be detected, and the cause of the error/problem may be determined by rotating the motor backwards. If no problem/error is detected (i.e., M₁≤Thershold₄), the drug delivery procedure can continue and the missing rotations may be compensated 602. In some embodiments, an error may be detected if the number of missing rotations M₁ is equal to or larger than Threshold₄, and no error is detected if M₁ is lower than Threshold₄.

When a problem/error is detected, the rotation of the motor may be reversed/inverted 612 so as to rotate the motor backwards. The rotation of the motor is monitored 614 as it is rotated backwards, and the number of missing rotations M₂ during such rotation is calculated 616. The motor activation 612, motor monitoring 614 and missing rotations calculation 616 may be performed in a manner similar to the operations 604, 606 and 608, respectively.

After the number of missing rotations during backward movement (M₂) is determined, it may be compared 618 to a threshold (e.g., Thershold₅). In some embodiments, this comparison determines if the error is due to occlusion or due to another cause (e.g., related to the driving mechanism). If the number of missing rotations M₂ equals to or is less than Thershold₅, i.e., no error is detected during backward rotation, indicating, for example, that there is no force that hinders the plunger movement backwards, it is determined 622 that occlusion has likely occurred. If, however, the number of missing rotations M₂ exceeds Thershold₅, i.e., an error is detected during both forward and backward movement, which may be indicative of interference to the driving mechanism movement in both directions, it is determined 620 that the error detected is due to a device malfunction, e.g., a malfunction associated with the driving mechanism and/or a component operatively coupled to it (e.g., a motor, a gear, a threaded rod, a nut, a sensor, a motor driver, etc.). In some embodiments, if the number of missing rotations M₂ exceeds Thershold₅, it may be indicative of a malfunction in the sensor monitoring the rotation of the motor. In some embodiments, an error may be detected during backward rotation if the number of missing rotations M₂ is equal to or larger than Threshold₅, and no error is detected if M₂ is lower than Threshold₅. After determining the type of error (occlusion or otherwise), a proper notification may be provided 624 to the user. It will be noted that the number of missing rotations M₂ may also refer to full motor rotations and/or to fractional rotations and/or to discrete motor steps. Further, the, values of the missing rotations M₁ and M₂, as well as Threshold₄ and Thershold₅, may depend on the resolution of the monitoring and on the encoder sensitivity, for example.

Calculating the number of rotations $N_1$ and/or the power provided to the motor may be based on at least one of, for example, the efficiency, frictional forces, inertia, and/or wear-and-tear of the device, according to some embodiments, and can be done using a known ratio, a formula, a lookup table, and the like. In some embodiments, Threshold$_4$ and/or Threshold$_5$ may be adjusted during the device lifetime, e.g., based on changes in the driving mechanism's efficiency, for example.

According to some embodiments, a certain deviation (e.g., 2%) between the calculated rotations and the actual rotations may not be considered to be an error. According to some embodiments, such deviation between the calculated rotations and the actual rotations, during forward rotation, may require further activation of the motor to achieve the calculated number of rotations, i.e., compensation. In some embodiments, the compensation may be carried out immediately after the deviation is detected, or the required compensation may be recorded in a memory and carried out later on.

According to some embodiments, the pattern of missing rotations (e.g., missing steps) may imply on an error and/or the cause of the error (error type). For example, missing steps at the same position in each cycle may imply on a deformed gear.

According to some embodiments, detecting an error and/or determining the error type may be based on the number of missing rotations (e.g., missing steps). In some embodiments, detecting an error and/or determining the error type may be based on a certain number of missing rotations (e.g., missing steps) occurring during a fixed number of motor rotations (e.g., 10 cycles, half a cycle), a fixed number of motor activations and/or a fixed duration (time) of motor activation (e.g., 10 min, 1 hour, etc.).

For example, an infusion device is programmed to deliver 0.5 U of insulin, which may require ten motor cycles. The device may include a stepper motor and twenty motor steps may be required to complete a full motor cycle. The threshold for error detection during forward rotation may be ten missing steps (cumulative) in ten motor cycles (e.g., Threshold$_4$=9.9), and the threshold for error detection in reverse rotation (i.e., the threshold which is the basis for determining the error type) may be, in this example, eight missing steps (cumulative) during ten motor cycles (e.g., Threshold$_5$=7.9). In this example, power is provided to the motor, and during the fifth cycle there are two missing steps ($M_1$=2), i.e., two of the pulses provided to the motor did not result in motor steps. Since the threshold for error detection is ten missing steps, no error is detected. The motor may then be reactivated and during the seventh cycle eight steps are missed. The updated missing steps count is $M_1$=10, as the currently eight missed steps are added to the two previously missed steps. Thus, an error is detected. The motor may then be rotated in reverse (backwards) for ten cycles, to maintain the same conditions under which the error was detected. The motor may otherwise be rotated in reverse any other number of cycles which is sufficient for error detection. In this example, throughout the ten cycles of the motor's inverted/reverse movement there are four missing steps ($M_2$=4). Thus, it is determined, in this example, that an occlusion condition exists, as no error was detected during reverse rotation of the motor ($M_2 \leq$ Threshold$_5$).

FIG. 8 shows an embodiment of an example error-detection procedure 700 that may be used to initiate a procedure for detecting the type of error, shown for example in FIGS. 5 and 7. The example error detection procedure 700 is based on faulty motor rotation, e.g., rotating the motor requires more power to accomplish than some pre-determined value. For example, if rotating the motor a full cycle requires 200 mW, a faulty rotation may be deemed to exist if the power requirement to complete a full motor cycle is less than 180 mW or above 230 mW. Under those circumstances, a proper rotation is deemed to exist when the power requirement is between 180 mW and 230 mW. In case a stepper motor is employed, the classification (faulty rotation/proper rotation) may be based on the number of missing steps.

The error detection procedure 700 may be performed whenever the motor is activated and/or whenever there is an irregular reading from the sensor monitoring the motor rotation (e.g., an encoder).

For example, first, the motor is activated 701, to deliver therapeutic fluid to the user's body. When there is a reading from the encoder 702 (e.g., periodically according to a predetermined time schedule, related to motor activation, related to a change in the delivery profile, etc.), power level value provided to the motor is received 704, e.g., from a fuel gauge, motor driver, by calculation and/or from another procedure. These parameters are compared 706 to determine whether the motor rotates properly or not. In some embodiments, the value received in step 704 may correspond to a number of pulses sent to the motor. In such embodiments, for example, the number of executed motor steps may be compared, at 706, to the number of pulses sent to the motor to determine the number of missing steps (i.e., pulses not resulting in steps). Depending on the result of the comparison 706, either the proper rotation counter, $\Sigma p$ or the faulty rotation counter, $\Sigma f$ is updated, at 708 and 710, respectively. Based on the values of the counters $\Sigma p$ and $\Sigma f$, an error may be detected 712. Error detection may be based, for example, on comparing at least one of the counters to a threshold and/or based on the correlation (or level of correlation) between the counters. For example, an error may be detected if the number of faulty rotations $\Sigma f$ is more than half of the number of proper rotations $\Sigma p$.

When error is detected, the cause for the error may be determined 714 by, for example, initiating error type determination procedures (e.g., procedure 90). In some embodiments, the procedure to determine the cause for the error may include operations similar to operations 702-712 of procedure 700. For example, upon error detection, the motor may be rotated in reverse a certain number of rotations, and the error type may be determined based on the number of faulty rotation and/or the number of proper rotations. Else, when no error is detected, stopping the motor from rotating may be considered. Since activation of the motor may result in the delivery of an additional amount of therapeutic fluid, determining whether or not the motor should be stopped may be based on the total amount of fluid which is to be delivered and/or the amount of fluid already delivered. In the circumstances where an additional amount of therapeutic fluid is to be delivered to the patient, the motor may be reactivated (if previously stopped) and/or remain active 702 and another iteration of procedure 700 may be executed. Else, when there is no need to deliver an additional amount of therapeutic fluid, the procedure is ended 718.

In some embodiments, the counters $\Sigma p$ and $\Sigma f$ may further be updated to remove older measurements and/or to reduce the relevancy of older measurements. The monitoring interval (window) may be fixed (e.g., an hour, 10 motor rotations) and/or variable and/or adaptive. For example, the monitoring interval may be time dependent (e.g., shorter during the night), and/or it may vary according to one or more of, for example, the amount of therapeutic fluid delivered, the flow rate (e.g., larger during bolus), power provided to the motor, encoder readings (e.g., the interval may be increased/decreased in case of abnormal readings), etc. For example, the monitoring window may include the last 0.05 ml of therapeutic fluid delivered to the user's body, and thus, the window may be considered variable with regard to its length (time) but fixed with regard to the movement of the driving mechanism.

The terms "power provided", "power consumed" and/or any other terms referring to the electrical charge that enables the rotation of the motor may refer to any of, for example, current, voltage, energy in their various forms (e.g., DC current, pulsed power) and/or a combination thereof.

Although several example embodiments of the procedures for detecting the cause of error/problem, and/or distinguishing occlusion related errors from other malfunctions are based on monitoring a motor's rotation, other parameters related to the therapeutic drug delivery can be monitored in addition to or instead of the motor's rotation, including, without limitation, at least one of, for example, flow rate, fluid temperature, movement of any of the driving mechanism's components, position of any of the driving mechanism's components, pressure inside the reservoir, motor's voltage, motor's current, motor's activation time, power consumption, plunger's position, plunger's movement, and the like.

The terms process, procedure and algorithm may be used interchangeably to describe embodiments of the error/problem detection procedures and the procedures to determine the cause of error (such procedures may be embodied in software and/or hardware). Furthermore, embodiments of the above mentioned procedures may include additional operations, and the operations may be performed in different orders and/or sequences. Also, one or more of the described operations may be omitted.

The controllers/processors described herein may include a controller, a CPU, a MCU, a memory device and/or a plurality of such components. Controllers, including processor-based device(s), may further include peripheral devices to enable input/output functionality. Alternatively and/or additionally, in some embodiments, special purpose logic circuitry, e.g., an FPGA (field programmable gate array) or an ASIC (application-specific integrated circuit) may be used in the implementation of the processor device(s).

Any and all references to publications or other documents, including but not limited to, patents, patent applications, articles, books, etc., presented in the present application, are herein incorporated by reference in their entirety.

Although a few variations have been described in detail above, other modifications are possible. For example, the logic flows depicted in the accompanying figures and described herein do not require the particular order shown, or sequential order, to achieve desirable results.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the embodiments and features disclosed herein. Other unclaimed embodiments and features are also contemplated. Accordingly, other embodiments are within the scope of the following claims.

What is claimed is:

1. A system for determining a problem in a fluid delivery device, the system comprising:
  a sensor configured to monitor at least one parameter associated with operation of the fluid delivery device; and
  a controller configured to:
    activate a motor of the fluid delivery device;
    detect an occurrence of a problem in fluid delivery based on one or more first sensor signals generated by the sensor when the motor is activated in a first direction, the one or more first sensor signals being representative of the at least one parameter monitored when the motor is activated in the first direction; and
    determine a type of the detected problem based on one or more second sensor signals generated by the sensor when the motor is activated in a second direction substantially opposite the first direction, the one or more second sensor signals being representative of the at least one parameter monitored when the motor is activated in the second direction;
  wherein the one or more first and second sensor signals comprise a number of rotations of the motor or a power consumption of the motor.

2. The system according to claim 1, wherein the controller is configured to:
  determine whether the one or more first sensor signals correlate with one or more first activation signals provided by the controller to activate the motor in the first direction; and
  determine whether the one or more second sensor signals correlate with one or more second activation signals provided by the controller to activate the motor in the second direction.

3. The system according to claim 1, wherein the motor is a stepper motor, a DC motor, a Shape memory alloy motor, or a SMA actuator.

4. The system of claim 1, wherein the one or more first and second sensor signals comprise a number of rotations of the motor and a power consumption of the motor.

5. The system of claim 4, wherein the detection of an occurrence of a problem by the controller comprises comparing the number of rotations of the motor to the power consumption of the motor to generate a first value and comparing the first value to a predetermined value.

6. A method of determining a problem in a fluid delivery device, the method comprising:
  monitoring with a sensor at least one parameter associated with operation of the fluid delivery device;
  detecting an occurrence of a problem in fluid delivery based on one or more first sensor signals generated when a motor of the fluid delivery device is activated in a first direction, the one or more first sensor signals being representative of the at least one parameter monitored when the motor is activated in the first direction; and
  determining a type of the detected problem based on one or more second sensor signals generated when the motor is activated in a second direction substantially opposite to the first direction, the one or more second sensor signals being representative of the at least one parameter monitored when the motor is activated in the second direction;
  wherein the one or more first and second sensor signals comprise a number of rotations of the motor or a power consumption of the motor.

7. The method according to claim 6,
  wherein the step of detecting the occurrence of the problem in fluid delivery comprises determining whether the one or more first sensor signals correlate with one or more first activation signals provided to activate the motor in the first direction; and
  wherein the step of determining the type of the detected problem comprises determining whether the one or more second sensor signals correlate with one or more second activation signals provided to activate the motor in the second direction.

8. The method according to claim 6, wherein detecting the occurrence of the problem in fluid delivery comprises:
determining a first ratio between a first value associated with activation of the motor in the first direction and a second value based on the one or more first sensor signals; and determining whether the first ratio exceeds a first threshold.

9. The method according to claim 8, wherein determining the type of the detected problem comprises:
determining a second ratio between a third value associated with activation of the motor in the second direction and a fourth value based on the one or more second sensor signals; and determining whether the second ratio exceeds a second threshold.

10. The method according to claim 8, wherein detecting the occurrence of the problem further comprises:
calculating a total number of occurrences that determined first ratios exceed the first threshold; and
determining whether the calculated total number of occurrences that the determined first ratios exceed the first threshold exceeds a third threshold.

11. The method according to claim 9, wherein determining the type of the detected problem further comprises:
calculating a total number of occurrences that determined second ratios exceed the second threshold; and
determining whether the total number of occurrences that the determined second ratios exceed the second threshold exceeds a fifth threshold.

12. The method according to claim 6, wherein the monitored at least one parameter is rotation of at least one of the motor and one or more gears.

13. The method according to claim 8, wherein at least one of the first value and the second value corresponds to a number of motor rotations, the number of motor rotations being an integer or a non-integer number greater than or equal to 0.

14. The method according to claim 13, wherein the first value corresponds to an expected number of motor rotations and the second value corresponds to a number of executed motor rotations.

15. The method according to claim 9, wherein at least one of the third value and the fourth value corresponds to a number of motor rotations, the number of motor rotations being an integer or a non-integer number greater than or equal to 0.

16. The method according to claim 15, wherein the third value corresponds to an expected number of motor rotations and the fourth value corresponds to a number of executed motor rotations.

17. The method according to claim 8, wherein at least one of the first value and the second value corresponds to a level of power consumed by the motor.

18. The method according to claim 9, wherein at least one of the third value and the fourth value corresponds to a level of power consumed by the motor.

19. The method according to claim 6, wherein the determined type of the problem includes one of: an occlusion in a delivery line of the fluid delivery device, a device malfunction, a motor malfunction, a deformations in the driving mechanism, a faulty encoder, an inefficient motor, a broken gear, a stuck gear, and a jammed gear.

20. The method according to claim 19, wherein the device malfunction is a driving mechanism malfunction.

21. The method according to claim 6, further comprising:
providing at least one notification to the user corresponding to one or more of the detection of the occurrence of the problem and the determined type of detected problem.

22. The method according to claim 6, wherein monitoring the at least one parameter comprises:
emitting light;
detecting the emitted light; and
periodically preventing the detection of the emitted light by blocking the emitted light.

* * * * *